(12) United States Patent
Daniel et al.

(10) Patent No.: US 6,907,357 B2
(45) Date of Patent: Jun. 14, 2005

(54) OUT-OF-MOLD INSPECTION OF FIBROUS PREFORM

(75) Inventors: Isaac M. Daniel, Morton Grove, IL (US); Sun Kyoung Kim, Hanam (KR)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/854,741

(22) Filed: May 26, 2004

(65) Prior Publication Data

US 2004/0267460 A1 Dec. 30, 2004

Related U.S. Application Data

(63) Continuation-in-part of application No. 10/611,318, filed on Jul. 1, 2003.
(60) Provisional application No. 60/394,007, filed on Jul. 3, 2002.

(51) Int. Cl.[7] .......................... G06F 19/00; B28B 17/00
(52) U.S. Cl. ......................................... 702/35; 425/149
(58) Field of Search ........................... 702/35; 425/149; 73/38

(56) References Cited

U.S. PATENT DOCUMENTS

| | | | | |
|---|---|---|---|---|
| 5,052,906 A | * | 10/1991 | Seemann | 425/112 |
| 5,295,800 A | * | 3/1994 | Nelson et al. | 425/130 |
| 5,972,256 A | * | 10/1999 | Wurst et al. | 264/40.1 |
| 6,143,215 A | * | 11/2000 | McCollum et al. | 264/40.1 |
| 6,375,449 B1 | * | 4/2002 | Seres et al. | 425/130 |
| 6,532,799 B2 | * | 3/2003 | Zhang et al. | 73/38 |

OTHER PUBLICATIONS

Starr et al., Measurement of Gas Transport Through Fiber Preforms and Densified Composites for Chemical Vapor Infiltration, 1998, J. Am. Ceram. Soc., vol. 81, No. 5, pp. 1298–1304.*
Ditkowski et al., Optimization of Chemical Vapor Infiltration with Simultaneous Powder Formation, Nov. 2000, ICASE Report No. 2000–44, NASA/CR–2000–210620.*
Dimension prediction and control for resin transfer molding process; Proceedings of SAMPE Conference; pp. 1–14; May 11–15, 2003; C. Dong et al.
Gas assisted real–time assessment of whole–field permeability profile of fiber preform for liquid composite molding processes; Proceedings of SAMPE Conference; pp. 1–13; May 11–15, 2003; C. Zhang et al.
Optimal control of accelerator concentration for resin transfer molding process; International Journal of Heat and Mass Transfer, vol. 46, pp. 3747–3754, 2003, S.K. Kim et al.

(Continued)

Primary Examiner—John Barlow
Assistant Examiner—Toan M. Le

(57) ABSTRACT

A fibrous preform such as a braided or stamped fibrous is inspected for a defect prior to placing the preform in a molding cavity by flowing gas through regions of the preform while it is located outside the molding cavity, measuring gas pressure at the regions, and determining deviations in measured gas parameter among the regions. The deviations of the gas parameter for a particular preform are compared to background data that includes deviations of the gas parameter determined for previously tested performs such that a relatively large deviation for a particular preform is considered to identify that preform as a defective preform as opposed to an acceptable preform.

33 Claims, 3 Drawing Sheets

OTHER PUBLICATIONS

Gas Flow Method for Detecting Local Preform Defects by Inverse Estimation of Space–varying Permeability; Journal of Composite Materials, vol. 37, No. 15, pp. 1367–1383, 2003, S.K. Kim et al.

Deterimination of three–dimensional permeability of fiber preforms by the inverse parameter estimation technique; Composites: Part A, vol. 34, pp. 421–429, 2003, S.K. Kim et al.

Determination of In–Plane Permeability of Fiber Preforms by the Gas Flow Method Using Pressure Measurements; Polymer Composites, vol. 24, No. 1, pp. 34–44, 2003, S.K. Kim et al.

Determination of permeability of fibrous medium considering inertial effects; Int. Comm. Heat Mass Transfer, vol. 29, No. 7, pp. 879–885, 2002, S.K. Kim et al.

Detection of local preform defects by gas flow method and statistical analysis; Advanced Composites Letters; vol. 12, No. 3, pp. 109–114, 2003, S.K. Kim et al.

In–Situ quality control of RTM preforms by the gas flow method; 48th International SAMPE Symposium, pp. 1702–1713, May 11–15, 2003.

Solution to inverse heat conduction problem in nanoscale using sequential method; Numerical Heat Transfer, Part B; vol. 44; pp. 439–456, 2003, S.K. Kim et al.

In–situ measurement and monitoring of fiber preform permeability for liquid composite molding; Proceedings of the 45th International SAMPE Symposium, vol. 45, p. 2053–2063, 2000, Z. Liang et al.

Gas flow method for detection of local preform defects based on statistical analysis; Proceedings of ICCM 14 Conference; pp. 1–8 Jul. 14–18, 2003; S.K. Kim and I.M. Daniel.

New set–up for measurement of permeability properties of fibrous reinforcements for RTM; Composites: Part A, vol. 33, pp. 959–969, 2002, K. Hoes et al.

Permeability Measurement and Flow Simulation Through Fiber Reinforcement; Polymer Composites, vol. 17, No. 1, pp. 34–42, Feb. 1996, R. Gauvin et al.

A control volume finite–element method for two–dimensional fluid flow and heat–transfer; Numerical Heat Transfer, vol. 6, pp. 245–261, 1983, B.R. Baliga et al.

A gas flow method for determination of in–plane permeability of fiber preforms; Polymer Composites, vol. 22, No. 1, pp. 47–56, 2001, M.K. Um et al.

Statistical characteristization of fiber permeability for composite manufacturing; Polymer Composites, vol. 21, No. 6, pp. 996–1006, Dec. 2000, R. Pan et al.

Gas flow test of Braided Preform Quality for Resin Transfer Molding; Advanced Composites Letters, vol. 12, No. 4, pp. 161–163, Sep. 2003, S.K. Kim et al.

* cited by examiner

OUT-OF-MOLD INSPECTION OF FIBROUS PREFORM

This application is a continuation-in-part of U.S. Ser. No. 10/611,318 filed Jul. 1, 2003, which claims the benefits of provisional application Ser. No. 60/394,007 filed Jul. 3, 2002.

CONTRACTUAL ORIGIN OF THE INVENTION

The United States Government may have rights in this invention pursuant to Contract No. N00014-02-C-0087 between the Office of Naval Research and Northwestern University, Evanston, Ill.

FIELD OF THE INVENTION

The present invention relates to inspection of a fibrous preform prior to placement in a molding cavity for making composite components or structures by a liquid molding process, such as resin transfer molding.

BACKGROUND OF THE INVENTION

The resin transfer molding (RTM) process has become a popular composite manufacturing process due to its suitability for high volume production and cost effectiveness. In this process, a dry fiber reinforcement (preform) is enclosed in the mold and resin is injected and allowed to cure. Resin injection or transferability is defined by the permeability of the preform and it can be severely affected by defects, distortions or anomalies in the preform. In some cases, such as those involving complex geometries, it is not uncommon for a relatively flexible (non-rigid) preform to be misplaced or to shift and be distorted during mold closure. For example, a draping, shearing, and/or folding defect of such preforms has been observed to occur during placement of the preform in the molding cavity. Such a defect, if not detected and corrected before resin injection, results in costly scrapping of the finished part. Such preform defects can cause local permeability non-uniformities and affect the resin flow resulting in local resin-starved areas. Furthermore, preform distortions could contribute to residual stresses and undesirable stress concentrations during subsequent loading in service.

The impregnation of the fluid into the preform is defined by the permeability of the reinforcement, which is the ability of a Newtonian fluid to permeate a porous medium with a sufficiently low Reynolds number, as given by Darcy's Law. The permeability of an undistorted preform with a constant fiber volume ratio can be assumed to be uniform over the entire domain; however, the permeability can be significantly altered by defects, distortions, or other anomalies in the preform. Such drastic changes in local permeability can affect resin flow patterns, rendering portions of the mold to be insufficiently filled. Permeability variations within a preform can be attributed to a number of factors, such as improper preform preparation, misplacement or shifting in the mold, accidental inclusion of foreign material, natural surface density variation of the preform, etc. If such occurrences were not detected prior to resin injection, the potential for costly part scrapping would be increased. Aside from the additional voids due to permeability non-uniformities, preform distortions could contribute to residual stresses and stress concentrations during in-service loading. Early detection, therefore, of such reinforcement irregularities is critical for effective quality control.

To avoid difficulties associated with use of flexible (non-rigid) preforms, relatively rigid braided or stamped fibrous performs have often been employed for resin transfer molding. Such performs are more solid-like and easier to place in the molding cavity without distortion of the preform. However, it is still important to detect defects and irregularities associated with such relatively rigid braided or stamped fibrous preforms as a quality control step for reducing costly scrapping and insuring the quality and reliability of fabricated composite structures.

SUMMARY OF THE INVENTION

The present invention relates to inspection of a fibrous preform residing outside a molding cavity for liquid composite molding (e.g. resin transfer molding) to make a composite component or structure. That is, the present invention involves inspecting a fibrous preform before it is placed in the molding cavity such that a defective preform is not used. The present invention is especially useful for inspecting relatively rigid braided or stamped fibrous performs for the presence of one or more defects and/or anomalies adversely affecting quality of the preform for molding, although the invention is not limited to such preforms.

One embodiment of the present invention involves inspecting a gas permeable fibrous preform prior to placing the preform in a molding cavity by flowing gas through regions of the preform while the preform is located outside the molding cavity, measuring a gas parameter at the regions, and determining deviations in the measured gas parameter among the regions. In an illustrative embodiment, gas pressure is measured as the gas parameter during constant rate gas flow. In another illustrative embodiment, gas flow rate is measured as the gas parameter during supply of the gas at substantially constant gas pressure. The gas can be flowed through the regions in succession one region after another or concurrently through the regions. In another embodiment, the deviations of the measured gas parameter for a particular preform are compared to background data that includes deviations of the gas parameter determined for previously inspected performs. A relatively large deviation of measured gas parameter for a particular preform relative to the data identify that particular preform as a defective preform not to be placed in the molding cavity.

In an illustrative embodiment of the present invention, the gas is flowed at a substantially constant flow rate through a channel formed on a surface of the preform and through the preform to an opposite surface thereof vented to ambient atmospheric pressure. The gas pressure is measured to determine gas pressure drop across a dimension of the preform for each of the regions. For example, the gas pressure drop across a thickness dimension is determined for each of the regions residing along a length dimension of the preform.

Still another embodiment of the present invention involves apparatus for inspecting a fibrous preform while it is disposed outside a molding cavity. The apparatus comprises gas channel-forming means for forming a chamber or channel on a surface of the preform, means for flowing gas into the channel, a gas parameter measuring device for measuring a gas parameter, and means for releasably disposing the gas channel-forming means on the preform while it is disposed outside the molding cavity.

Advantages and details of the present invention will be more readily apparent from the following detailed description taken in conjunction with the following drawings.

DESCRIPTION OF THE INVENTION

For purposes of illustration and not limitation, the invention will be described with respect to inspection of a fibrous preform residing outside a molding cavity (not shown) of the type used for liquid composite molding (e.g. resin transfer molding) to make a composite component or structure. Such a molding cavity is described and shown in copending application Ser. No. 10/611,318 filed Jul. 1, 2003,the teachings of which are incorporated herein by reference. The present invention thus involves inspecting a fibrous preform before it is placed in the molding cavity such that a defective preform can be discarded and not placed in the molding cavity for liquid molding, thereby reducing costly scrapping and insuring the quality and reliability of molded composite structures. The fibrous preform can be inspected for the presence of defects and/or anamolies present in the internal preform structure that may yield defects in the molded composite structure. The invention thereby provides quality control inspection of fibrous performs prior to their use in a liquid molding process.

Although the invention will be described herebelow with respect to inspection of a relatively rigid fibrous preform, the invention is not so limited and can be practiced in connection with inspection of various types of fibrous preforms that are gas permeable. Relatively rigid, gas permeable fibrous performs include performs that are substantially self-supporting with little preform flexibility and include braided performs, stamped performs, knitted, and stitched preforms. In comparison, relatively non-rigid, gas permeable fibrous performs can include fiber mats, fiber layers, and woven fabrics that are not self-supporting and exhibit substantial preform flexibility.

Figure 1:
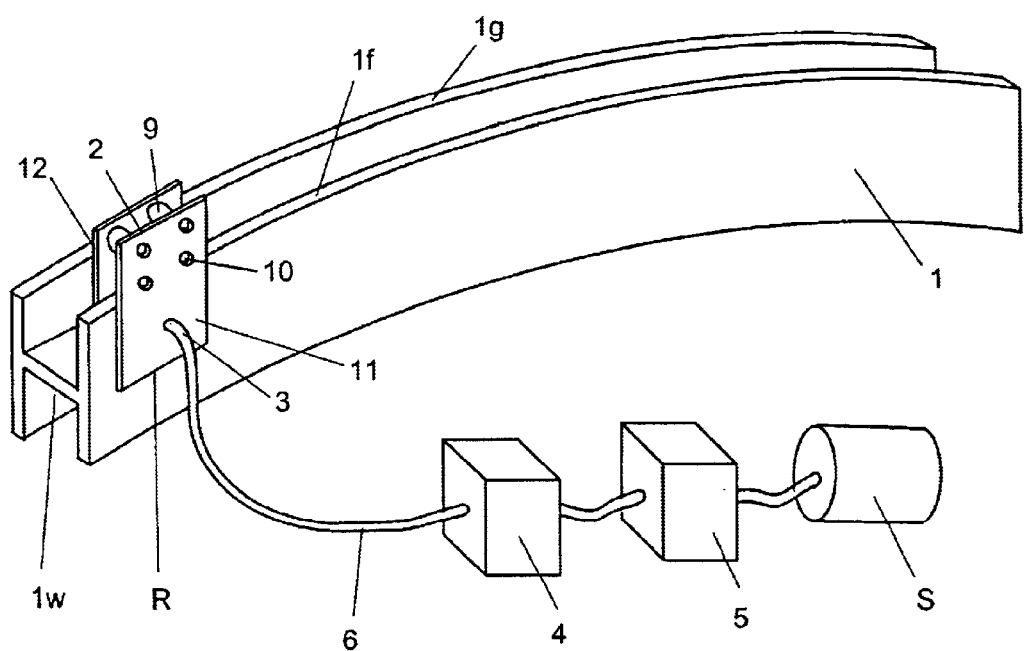
FIG. 1 is a schematic view of apparatus for practicing a method embodiment of the invention for inspecting a fibrous preform while it is disposed outside a molding cavity.
Figure 2:
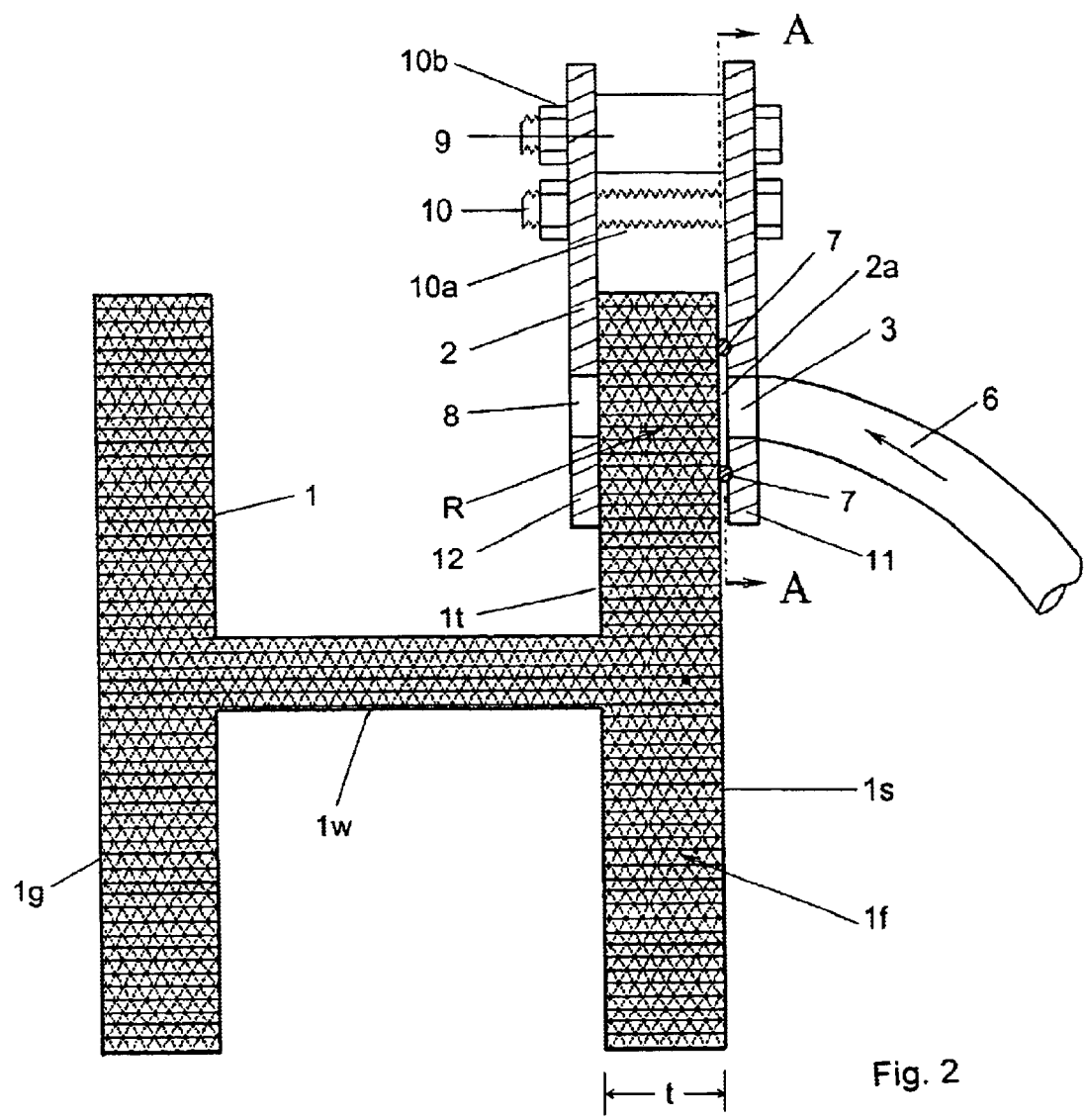
FIG. 2 is a sectional view of a braided fibrous preform being inspected using inspection apparatus pursuant to an embodiment of the invention. One spacing collar 9 is omitted for convenience to reveal threaded bolt 10a therein.
Figure 2A:
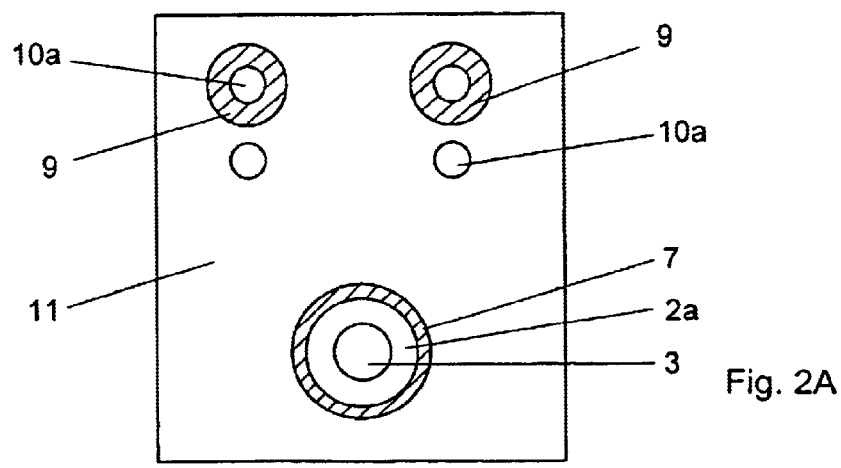
FIG. 2A is a sectional view taken through section A—A of FIG. 2.

FIGS. 1, 2 and 2A illustrate schematically a relatively rigid, gas permeable fibrous preform 1 being inspected prior to placement in a molding cavity pursuant to an embodiment of the invention. For example, the preform 1 can comprise a braided or stamped preform mentioned above. In particular, preform inspection is conducted using inspection apparatus having gas channel-forming means 2 that forms a gas-receiving chamber or channel 2a on a surface 1s of the preform 1 and means for flowing an inspecting gas to the channel 2a. For purposes of illustration and not limitation, the gas channel-forming means 2 is shown as a fixture comprising first and second plates 11, 12 disposed on opposite sides of flange 1f of the preform 1 and an O-ring seal 7 disposed between plate 11 and surface is of the preform to form gas-receiving channel 2a. The plates 11, 12 are releasably held on the preform flange by clamping fasteners 10 such as threaded bolts 10a and nuts 10b which are tightened to clamp the inspection plates 11, 12 on the flange surfaces. Spacing collars 9 reside between the plates 11, 12 about each bolt 10a to control clamp force applied on the flange surfaces 1s, 1t. When the inspection apparatus is clamped on the flange surfaces as shown in FIGS. 1 and 2, the O-ring seal 7 is compressed in gas tight manner between the preform surface 1s and the plate 11 to form gas-receiving channel 2a.

The means for flowing gas into the channel 2a preferably comprises a source S of the gas connected to channel 2a by a gas supply conduit 6 and a flow meter 5 and pressure measuring device 4 in conduit 6 between the source S and the channel 2a. The flow meter 5 provides a substantially constant flow rate of the gas to channel 2a. For purposes of illustration and not limitation, the source S of the gas can comprise a conventional high pressure cylinder of nitrogen or air. The flow meter 5 can comprise a conventional gas flow controller (model FMA-2407 or FMA-A2401 gas flow controller sold by Omega Engineering, Inc.).

The gas pressure measuring device 4 is shown communicating to the channel 2a via conduit 6 for measuring gas pressure. For purposes of illustration and not limitation, the gas pressure measuring device 4 can comprise a conventional differential pressure transducer.

An illustrative embodiment of the invention involves inspecting successive local areas or regions R of the preform along a dimension thereof. For example, FIGS. 1 and 2 illustrate inspection of the thickness dimension t of a local flange area or region R of the preform 1 while the preform is located outside a molding cavity. After this local area or region R is inspected, the next successive local area or region located a selected incremental distance along the length will be similarly inspected and so on until the overall length dimension of the preform flange is inspected. The same inspection approach can be applied to inspect the other preform flange 1g as well as the web 1w interconnecting the flanges 1f, 1g. The same inspection approach also can be applied to inspect an overall width or other dimension of a preform as required by preform geometry.

In conducting the inspection at each local region R using apparatus pursuant to an embodiment of the invention, the inspecting gas (e.g. nitrogen) is flowed at a substantially constant flow rate through a gas inlet 3 into channel 2a formed on preform surface 1s at the particular local region R and through the preform thickness t to an opposite preform surface it that is communicated or vented by opening 8 in plate 12 to ambient atmospheric pressure. The length and width of chamber 2a define the length and width of the local area or region tested on the preform. The gas pressure is measured by the pressure transducer 4 to determine gas pressure drop across the preform thickness dimension t at each of the local regions R (where the chamber 2a defines a length and width of the tested preform area) such that deviations or fluctuations of the gas pressure drop through the preform thickness among the local regions R can be determined. The pressure drop during constant rate gas flow through the preform thickness at the local areas or regions R is associated with the quality of the preform 1.

The deviations of the measured gas pressures for a particular preform 1 can be compared in a further embodiment of the invention to background gas pressure data that includes deviations of the gas pressures determined for previously inspected preforms. A relatively large deviation of measured gas pressures for a particular preform 1 relative to the data identify that particular preform as a defective preform not to be placed in the molding cavity, and instead to be discarded. For purposes of illustration, the measured gas pressure data can be accumulated for a plurality of previously inspected preforms 1, and the accumulated data can be statistically analyzed to provide preform quality control criterion for determining an acceptable versus defective preform in subsequent quality control inspections pursuant to the invention.

The following example is offered to further illustrate the invention but not limit it.

EXAMPLE

FIG. 1 shows a curved I-beam braided fiber preform 1 being inspected. Two different curved I-beam braided fiber preforms were inspected. One preform was designated A while the other preform was designated B. Both preforms A and B comprised carbon fibers three-dimensionally braided to form the curved I-beam shape but preform B was of a lower overall quality than preform A.

The inner radius and the angle or arc of each of the curved I-beam performs A and B were 0.556 inch and 120 degrees, respectively. The pressure drop through the thickness of the preform flange 1f of each preform was measured at selected intervals along the arc (angle of 120 degrees) of each preform.

The test apparatus comprised gas flow meter 5 to provide nitrogen gas at a constant flow rate of $3.17 \times 10^{-5}$ m$^3$/s and at ambient temperature through flexible conduit 6 connected to gas-channel forming means 2 as shown in FIG. 2 and as described above. A differential pressure transducer 4 was used to measure gas pressure and thereby determine pressure drop at each local area or region tested along the arc of each preform flange 1f. A strain gage panel meter (not shown such as a Model DP25-E-A available from Omega Engineering, Inc.) was used to provide excitation to the pressure transducer 4 and give a digital pressure output. The uncertainty of the pressure measurement with this system was calculated to be less than 1% from the accuracies of the pressure transducer and panel meter. The repeatability of the experiments performed using this equipment was considerably high, with negligible variation between tests.

Figure 3:
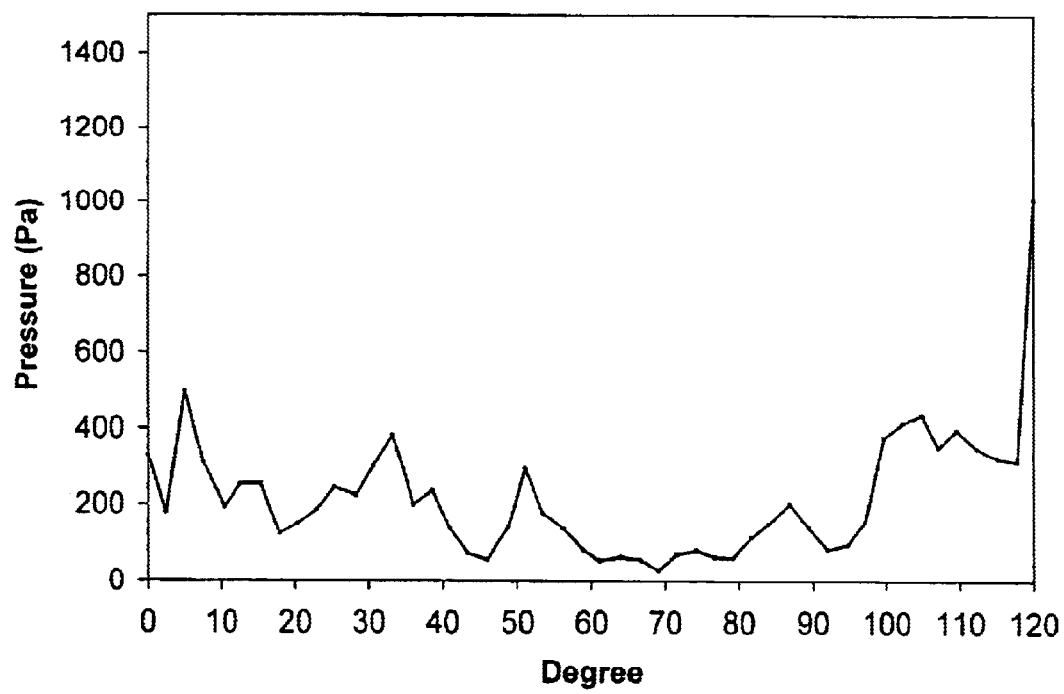
FIG. 3 is a graph of measured gas pressure versus location along the arc length of the braided preform of the type shown in FIG. 2 wherein the deviations of gas pressure are considered to indicate an acceptable preform for liquid molding.
Figure 4:
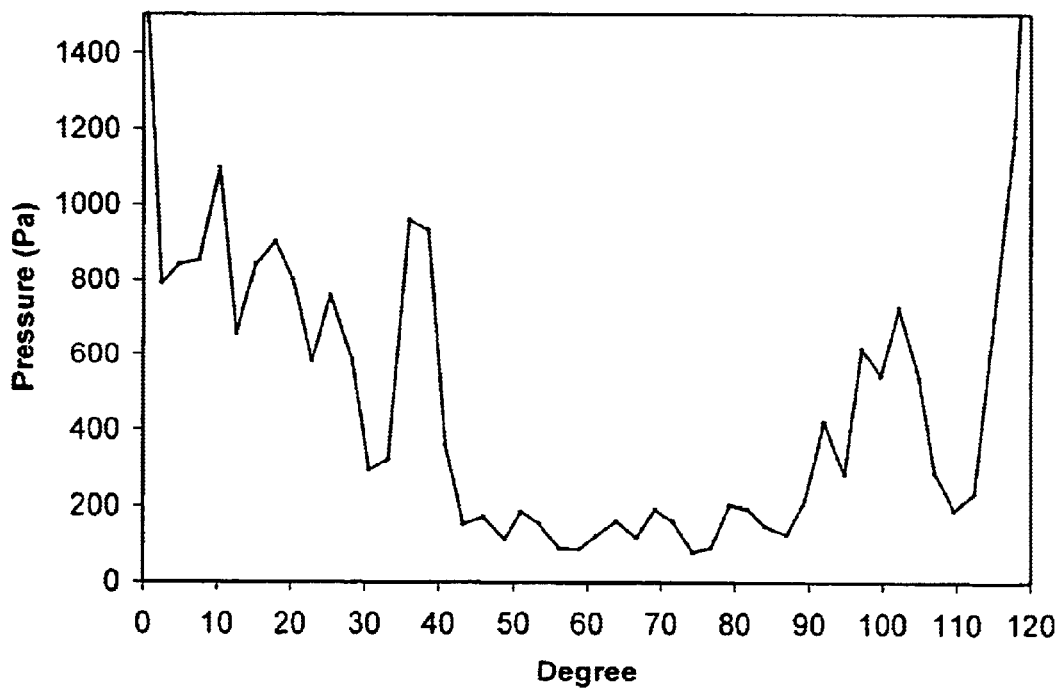
FIG. 4 is a graph of measured gas pressure versus location along the arc length of a different braided preform of the type shown FIG. 2 wherein the relatively large deviations of gas pressure (compared to FIG. 3) are considered to indicate an unacceptable, defective preform not to be placed in the molding cavity but, instead, discarded.

Results of the test inspections are shown in FIGS. 3 and 4 for preforms A and B, respectively, wherein the arc of each preform was inspected at intervals or increments of 2.5 degrees. It is apparent that the pressure drop varies noticeably along the arc for both preforms A and B. This indicates that the permeability of the preforms changes drastically from location to location along the arc. The pressure drop variation is much more pronounced at the ends of the preforms. The variation or deviation of pressure drops was more significant for preform B in FIG. 4 than for preform A in FIG. 3. The gas pressure deviations observed for preform A are normal and acceptable based on empirical RTM tests with known normal performs. In contrast, the pressure deviations observed for preform B are exceptionally large and abnormal, providing reason to consider preform B defective and not to be used in a subsequent liquid molding (RTM) process.

The invention thereby provides quality control inspection of fibrous performs prior to their use in a liquid molding process to reduce costly scrapped molded composite structures.

Although the invention has been described with respect to inspecting successive local areas or regions R along the length (e.g. arc length) of the preform, the invention is not so limited and envisions using a plurality of test apparatus similar to those described above concurrently placed along the length (or other dimension) of the preform to concurrently measure gas pressure drops through the thickness (or another dimension) of the preform at a plurality of local areas or regions R. In this way, the inspection of the fibrous preform at a plurality of intervals or increments along a dimension thereof may be facilitated.

Moreover, the invention envisions forming a single gas-receiving chamber or channel 2a along a dimension of the perform and providing a plurality of pressure measuring devices 4 communicated to the single channel at a plurality of regions R along the dimension of the preform to concurrently measure pressure drops at the regions R while gas is flowed at constant volume flow rate to the single chamber and through the perform.

Although the invention has been described above with respect to inspecting local areas or regions R of the perform by measuring gas pressure as a gas parameter at a constant rate gas flow, the invention is not so limited and envisions another embodiment involving measuring another gas parameter to this end. For example, the invention envisions measuring gas flow rate (as a gas parameter) at the local regions R while the inspection gas is supplied at constant pressure to the gas channel-forming means 2 of FIGS. 1, 2, and 2A (i.e. to gas-receiving chamber or channel 2a). A suitable gas flow rate measuring device for use in this embodiment of the invention can comprise a gas flow meter (Model FMA-A2305 available from Omega Engineering, Inc.) communicated to gas supply conduit 6. The inspection gas can be supplied at a constant pressure to the local regions R of the perform using a nitrogen gas cylinder (gas supply device) connected to gas supply conduit 6.

Although the invention has been described above in connection with certain embodiments thereof, those skilled in the art will appreciate that various changes, modifications, and the like can be made therein without departing form the spirit and scope of the invention as set forth in the appended claims.

We claim:

1. A method of inspecting a gas permeable fibrous preform for a defect prior to placing the preform in a molding cavity, comprising flowing gas through regions of the preform while the preform is located outside the molding cavity, measuring a gas parameter at the regions, and determining deviations in the measured gas parameters among the regions.

2. The method of claim 1 wherein the gas is flowed at a substantially constant flow rate and gas pressure is measured as the gas parameter.

3. The method of claim 1 wherein the gas is supplied at a substantially constant pressure and gas flow rate is measured as the gas parameter.

4. The method of claim 1 wherein the gas is flowed through the regions of the preform in succession one region after another.

5. The method of claim 1 wherein the gas is flowed through the regions of the preform in concurrent manner.

6. The method of claim 1 wherein the gas is flowed though a channel formed on a surface of the preform and then through the preform.

7. The method of claim 6 wherein the channel is formed in part on the surface by a seal.

8. The method of claim 6 wherein a second surface opposite from said surface of the preform is vented to ambient pressure.

9. The method of claim 2 wherein gas pressure drop across a dimension of the preform is determined for each of the regions.

10. The method of claim 9 wherein the gas pressure drop across a thickness dimension is determined for each of the regions.

11. The method of claim 2 wherein the gas pressure drops are determined for each of the regions along a length dimension of the preform.

12. The method of claim 1 including the additional step of comparing the deviations of the measured gas parameter for a particular preform to background data that includes deviations of the gas parameter determined for previously tested performs.

13. The method of claim 12 wherein a relatively large deviation of the measured gas parameter of the particular preform relative to the data identify said particular preform as a defective preform.

14. The method of claim 1 wherein the preform is a relatively rigid preform.

15. The method of claim 14 wherein the preform is a braided, stamped, knitted, or stitched fibrous preform.

16. A method of inspecting a gas permeable fibrous preform for a defect prior to placing the preform in a molding cavity, comprising flowing gas through a region of the preform while the preform is located outside the molding cavity, measuring a gas parameter at the region, and using the measured gas parameter to determine whether a perform is acceptable or not.

17. The method of claim 16 wherein the gas is flowed at a substantially constant flow rate and gas pressure is measured as the gas parameter.

18. The method of claim 16 wherein the gas is supplied at a substantially constant pressure and gas flow rate is measured as the gas parameter.

19. The method of claim 16 wherein the gas is flowed though a channel formed on a surface of the preform and then through the preform.

20. The method of claim 19 wherein the channel is formed in part on the surface by a seal.

21. The method of claim 19 wherein a second surface opposite from said surface of the preform is vented to ambient pressure.

22. The method of claim 17 wherein gas pressure drop across a dimension of the preform is determined.

23. The method of claim 22 wherein the gas pressure drop across a thickness dimension is determined.

24. The method of claim 16 wherein the preform is a relatively rigid preform.

25. The method of claim 24 wherein the preform is a braided, stamped, knitted, or stitched fibrous preform.

26. Apparatus for inspecting a fibrous preform disposed outside a molding cavity, comprising gas channel-forming means for forming a gas-receiving channel on a surface of the preform, means for flowing gas to the channel, a gas parameter measuring device for measuring a gas parameter, and means for releasably disposing the gas channel-forming means on the preform while it is disposed outside the molding cavity.

27. The apparatus of claim 26 wherein the gas channel-forming means comprises first and second plates clamped on opposite sides of the preform.

28. The apparatus of claim 26 wherein the gas parameter measuring device comprises a gas pressure measuring device communicated to a gas supply conduit connected to the gas-receiving channel.

29. The apparatus of claim 28 including a gas flow meter for providing a constant flow rate of the gas to the gas-receiving channel.

30. The apparatus of claim 26 wherein the gas parameter measuring device comprises a gas flow rate measuring device communicated to a gas supply conduit connected to the gas-receiving channel.

31. The apparatus of claim 30 including a gas supply device for providing the gas at substantially constant pressure to the gas-receiving channel.

32. The apparatus of claim 26 including means for venting an opposite surface from said surface of the preform to ambient pressure.

33. The apparatus of claim 32 wherein the means for venting comprises an opening in a plate clamped on the preform.

* * * * *